United States Patent [19]

Meyers

[11] Patent Number: 5,420,161

[45] Date of Patent: May 30, 1995

[54] DOISYNOLIC ACID TYPE COMPOUNDS AS WEIGHT AND APPETITE SUPPRESSING AND CONTROL AGENTS

[76] Inventor: Cal Y. Meyers, Southern Illinois University at Carbondale, Carbondale, Ill. 62901-4409

[21] Appl. No.: 98,853

[22] Filed: Jul. 29, 1993

[51] Int. Cl.[6] .................................................. A61K 31/19
[52] U.S. Cl. ....................................... 514/569; 514/570
[58] Field of Search ................................ 514/569, 570

[56] References Cited

PUBLICATIONS

Donohoe and Stevens, "Modulation of Food Intake by Hypothalamic Implants of Estradiol Benzoate, Estrone, Estriol and CI–628 in Female Rates[1]", Pharmacology Biochemistry & Behavior, vol. 16, 1982, pp. 93–99.

Meyers, et al, "Doisynolic–Type Acids—Uterotropically Potent Estrogens Which Compete Poorly with Estradiol for Cytosolic Estradiol Receptors", J. steroid Biochem. vol. 31, No. 4A, 1988, pp. 393–404.

Soto, et al, "How Many Rings Can be Cleaved From a Steroidal Estrogen While Preserving Its Estrogenic Activity?" The Endocrine Society, 70th Annual Meeting, Abstract of Paper No. 1301, Jun. 1988.

Meyers and Kolb, "Facile and Selective Chlorination—Cleavage of Some Cyclanones and Cyclanols with the $CCl_4$–KOH–t–BUOH Reagent. In Situ Conversion of Estrones and Estradiols into Dichlorodoisynolic Acids[1a]", J. Org. Chem., 1979, 44 (21), 3739, vol. 43, 1985 (1978), pp. 1985–1990.

Chemical Abstracts 67:40608u (1967).
Chemical Abstracts 75:128430f (1971).

*Primary Examiner*—Raymond Henley, III
*Attorney, Agent, or Firm*—Cushman, Darby & Cushman

[57] ABSTRACT

The present invention relates to a method of weight and appetite suppression in an animal, including humans, in need of such treatment, by administering an effective amount of the (+), the (−) or the (±) forms of one of the following compounds or derivatives thereof:

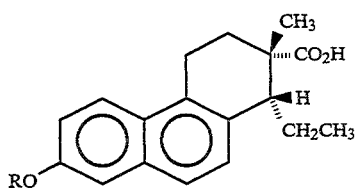

I

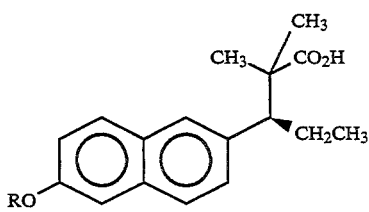

II

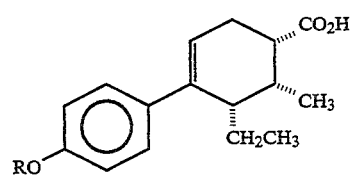

III

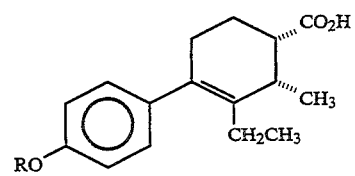

IV

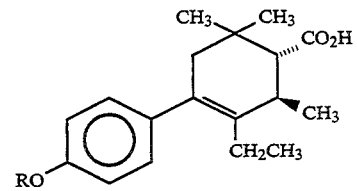

V (Abstract continued on next page.)

-continued
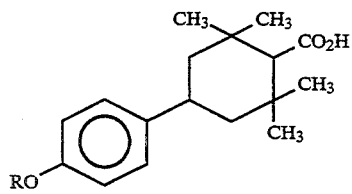
VI
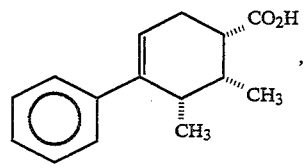
VIII
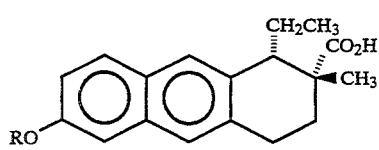
VII
and
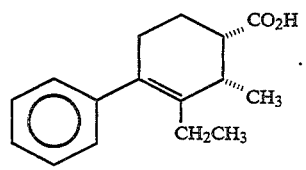
IX
8 Claims, No Drawings

DOISYNOLIC ACID TYPE COMPOUNDS AS WEIGHT AND APPETITE SUPPRESSING AND CONTROL AGENTS

FIELD OF THE INVENTION

The present invention relates to a method of promoting weight control and appetite suppression by administering an effective amount of a doisynolic acid compound to an animal, including humans, in need of such treatment.

BACKGROUND OF THE INVENTION

Estrogens, such as estradiol, have been well known for their promotion of rapid weight gain. As such, they have been commercially marketed as food additives, suitable for use in "fattening" animals more quickly. These additives have been used, for example, to increase weight in animals before they are slaughtered, in order to provide more meat from a single animal.

Donohoe and Stevens have published results which suggest that the mode of administration of estrogens may be responsible for the observed effects on weight. T. P. Donohoe, et al., Pharm. Biochem., 16, 93–99, 1982. Donohoe et al. implanted ovariectomized rats with crystalline estradiol benzoate, estrone or estriol using cannulae. This implantation was aimed at the ventromedial nucleus-arcuate region of the hypothalamus. Administration in this manner caused significant reduction in food intake and body weight for these rats, in contrast to the weight gain generally observed from the use of these compounds. In contrast, however, dorsal and lateral implantation of these compounds in the rats were generally ineffective in promoting weight loss. Thus, the effect of estradiol appears to be specific to the method of implantation. No oral administration was tested by Donohoe. Finally, it should be pointed out that these rats were ovariectomized animals, it can not be assumed that these results would be equally applicable to animals with intact ovaries.

The use of estrogens has significant drawbacks, as estrogens such as DES are known to be carcinogens and teratogens, and estradiol, when administered at therapeutic doses, is suspected to have carcinogenic properties. Thus, it was desirable to obtain compounds which mimicked the properties of the previously known estrogen compounds, without displaying the adverse side effects which they were known or suspected to possess.

Doisynolic acid compounds are known compounds which have been shown to have estrogenic properties in vitro. Meyers, et. al., J. Steroid Biochem, Vol. 31, pgs 393–404 (1988), herein incorporated by reference, discloses a variety of doisynolic acids. These compounds were found to exhibit no toxicity or carcinogenicity in mice, even though each of the doses which was administered was at least 1000 times the dose required for detectable estrogenic effects. In control studies, mice which were similarly treated with known carcinogens developed easily detected tumors. Meyers, J. Steroid Biochem, supra.

SUMMARY OF THE INVENTION

The present invention provides a method of controlling weight and suppressing appetites by administering to an animal, including humans, in need of such treatment an effective amount of the (+), the (−) or the (±) form of a compound of formula:

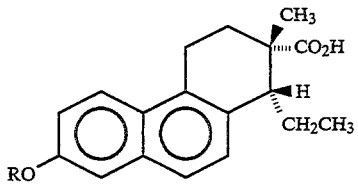

I

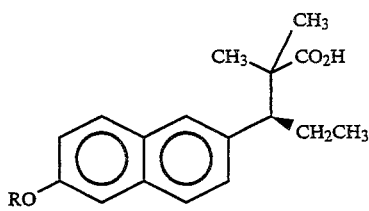

II

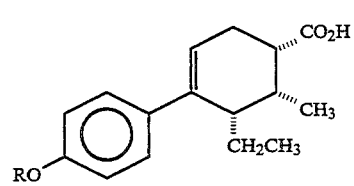

III

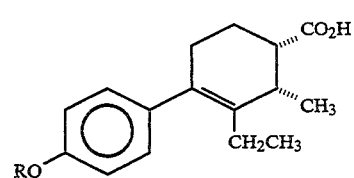

IV

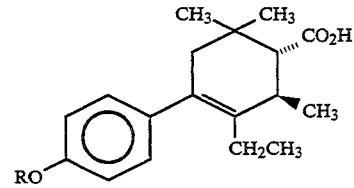

V

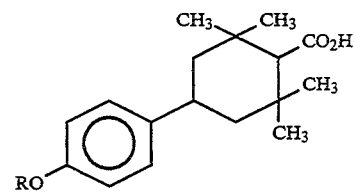

VI

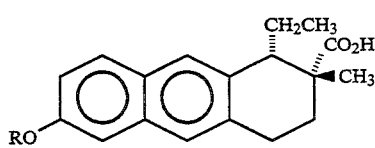

VII

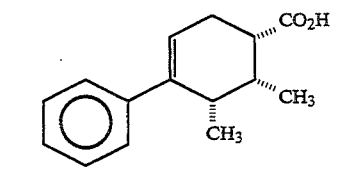

VIII

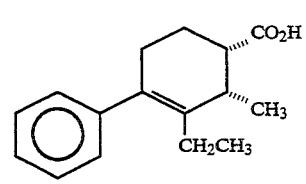

IX wherein R is selected from H, alkyl, alkenyl, benzyl, acyl, and the like.

These compounds can be administered as the free carboxylic acid, or as the salt or ester of the carboxylic acid. Furthermore, they may be combined with suitable pharmaceutical carriers for administration.

DETAILED DESCRIPTION OF THE PREFERRED EMBODIMENTS

The present invention provides for a method of inducing weight reduction and suppressing appetite in humans and other animals, by the administration of an effective amount of a doisynolic acid compound.

It was found that doisynolic acid compounds having the following formulae, when administered to animals, induced significant weight loss. This result was contrary to expectations, since, as noted above, doisynolic acid compounds are known to possess estrogenic activity, and estrogenic compounds were known to promote weight gain, not weight loss.

Compounds which are suitable for use in the presently claimed method are those selected from the (+), (−), or the (±) form of the following compounds:

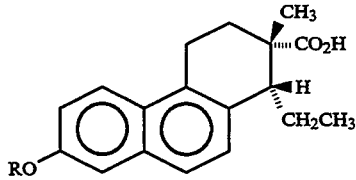

I

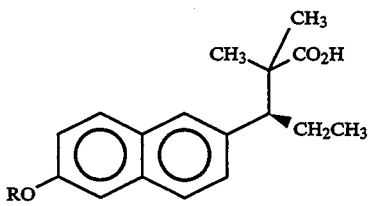

II

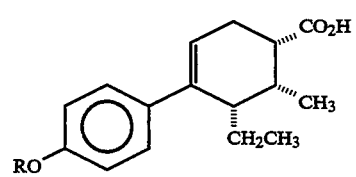

III

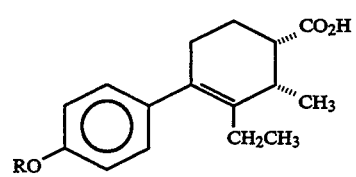

IV

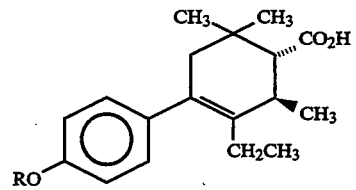

V

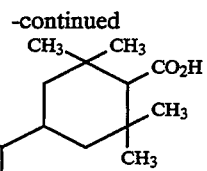

VI

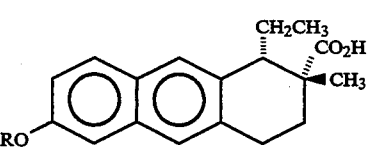

VII

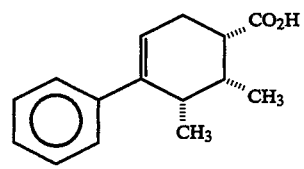

VIII

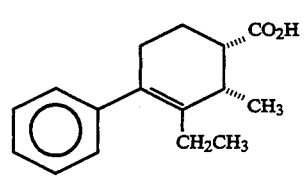

IX wherein R is selected from H, alkyl, alkenyl, benzyl, acyl and the like.

Preferred compounds include

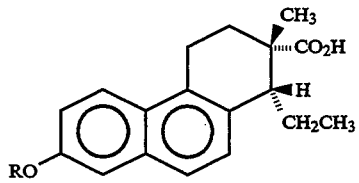

I wherein R is selected from H or $CH_3$. These compounds can be administered as the free carboxylic acid, as a pharmaceutically acceptable salt, or as the ester of the free carboxylic acid.

The doisynolic acid compounds set forth above can be commercially synthesized, and have been synthesized by a variety of known methods, see, e.g., the articles cited in Meyers, J. Steroid Biochem, supra. These articles are also incorporated by reference.

The compounds can be administered to humans and other animals in amounts which are effective to promote the desired weight loss or appetite suppression. Selection of the dosage or the appropriate amount of agent for treatment is well within the ordinary skill of the art.

The compounds may be administered by any appropriate method, including orally or by injection, and may be compounded with an appropriate pharmaceutical carrier for ease of administration.

The following working example demonstrates the application of the claimed invention, but the claimed invention should not be viewed as limited thereto, and one skilled in the art may easily envision other applications within the scope of the claimed invention.

EXAMPLE 1

BDDA methyl ether, a compound of formula I, where R is methyl, was administered subcutaneously to female Charles River CD1 mice. The weight gain or loss of the mice was monitored over a 13 day period, and the results were compared to that of vehicle injected controls. An appropriate positive control was included as well.

The mice used in the experiment were Charles River CD1 mice which were supplied at 28/29 days of age and had a weight in the range 18–20 grams. The animals were placed in a constant environment room, and were fed water and a small animal diet. On day 9, the animals were identified by tail marking, weighted, and assigned to one of three weight band groups, low, medium or high. The animals were placed in groups of 5 within their weight band. The animals were weighed on day 12, and then daily thereafter, except for weekends. On days 15, 16, and 17, a familiarizing injection which contained a vehicle, but no active compound, was provided to the mice.

On day 18, treatment with the BDDA-methyl ether commenced. The compound is provided to a treatment group containing 15 animals (5 high, 5 medium and 5 low). In addition, a negative control of 20 mice (5 high, 10 medium, 5 low) was formed. Dosing of the animals commenced on day 18 and continued until day 31. The results of the test are shown below in Table 1. Those mice which were treated with 5 μg/day of BDDA-methyl ether showed a weight loss of 34%, compared to the control mice. Those mice which were treated with 50 μg/day of BDDA-methyl ether showed a weight loss of 145%.

EXAMPLE 2

The procedure of Example 1 was carried out, except that the free phenol form of BDDA was used to treat the mice. This compound has the structure shown in formula I, where R is hydrogen. Treatment of the mice with this compound resulted in weight loss of 34% at a dosage level of 5 μg/day. Treatment of mice with 50 μg/day resulted in weight loss of 113% compared to the control.

Comparative Example 1

The procedure of Example 1 was carried out, except that the mice were administered estradiol, a compound of formula X, set forth below.

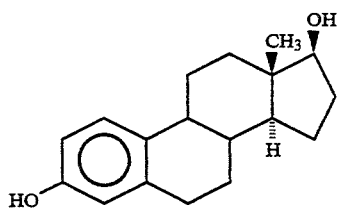

Mice which were treated with this compound at a dosage level of 5 μg/day displayed a weight gain of 55% compared to the control mice.

Comparative Example 2

The procedure of Example 1 was carried out, except that the mice were administered 16,16-dichlorodoisynolic acid-3-methyl ether. (Formula XI).

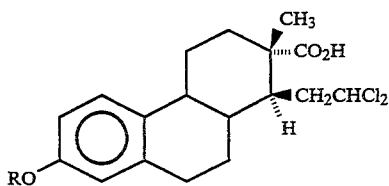

wherein R is $CH_3$. This compound, when provided at a dosage of 50 μg/day, caused weight gain of 20% over the control mice.

This compound is the most weakly estrogenic of the doisynolic acid compounds. The claimed compounds are believed to mimic the behavior of compound I, as unlike these compounds only compound XI can undergo ring closure to allow it to simulate the estradiol structure and weakly mimic its weight promoting ability.

The data for Examples 1 and 2, and comparative Examples 1 and 2, are set forth in Table I below.

TABLE 1

| Compound | Mouse Growth (Weight gain/loss)[1] | | | |
| --- | --- | --- | --- | --- |
| | Relative estrogenic potency | Dose (μg/ mouse/ day) | Wt. gain/loss, % difference from control | Sig. of difference (p < ...) |
| (+) Estradiol (X) | 1 | 5 | +55.0 | 0.001*** |
| (±) I, R=$CH_3$ | 1 | 5 | −34.2 | 0.005* |
| | | 50 | −145.1 | 0.0001*** |
| | | 500 | −166.7 | 0.001*** |
| (±)I, R=H | 1 | 5 | −33.9 | 0.05* |
| | | 50 | −112.6 | 0.001*** |
| | | 500 | −188.9 | 0.001*** |
| (+)XI, R=$CH_3$ | 0.1 | 50 | +20.3 | N.S. |

[1]See Example 1 for testing protocol.

What is claimed is:

1. A method of producing weight loss in warm blooded animals, comprising administering orally or by subcutaneous injection to the animal an effective amount of the (+), (−), or the (±) form of a compound selected from the group consisting of

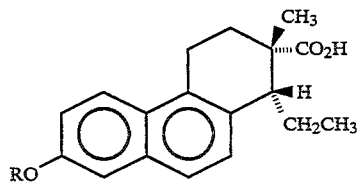

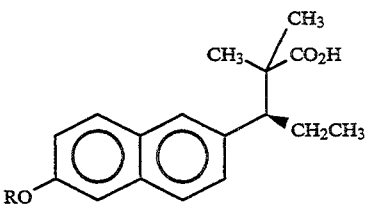

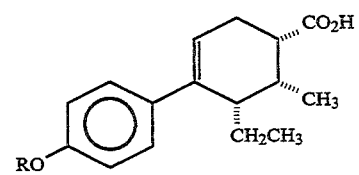

-continued

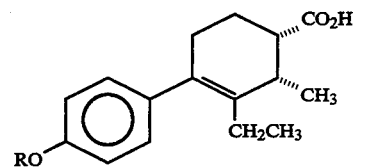 IV

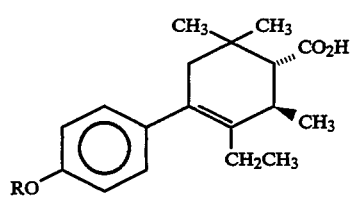 V

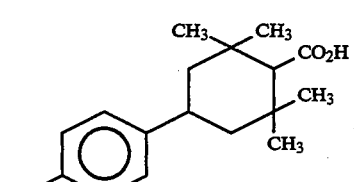 VI

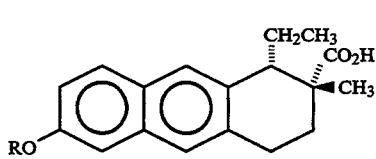 VII

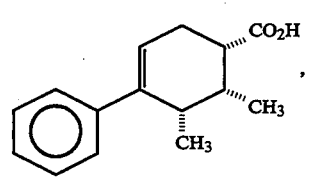 VIII and

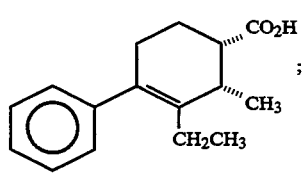 IX

;

wherein R is selected from H, alkyl, alkenyl, acyl, and benzyl; and wherein said compounds are present as the free carboxylic acid, a pharmaceutically acceptable salt, or an ester of the carboxylic acid.

2. A method according to claim 1, wherein R is selected from H and $CH_3$.

3. A method according to claim 1, wherein the compound is administered with a pharmaceutically acceptable carrier.

4. A method of suppressing appetites in warm blooded animals, comprising treating the animal orally or by subcutaneous injection with the (+), the (−) or the (±) form of a compound selected from the group consisting of

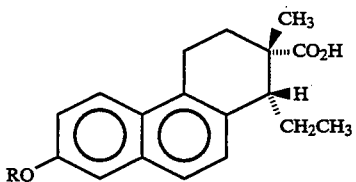 I

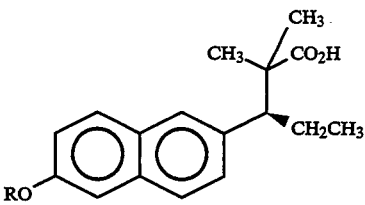 II

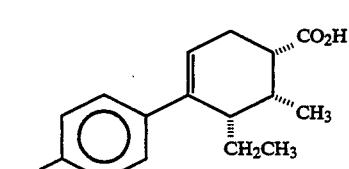 III

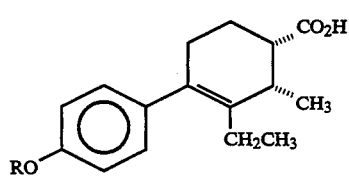 IV

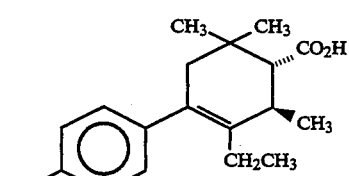 V

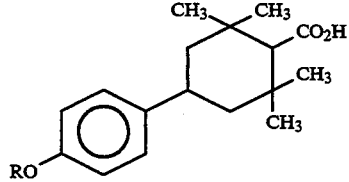 VI

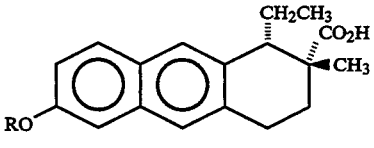 VII

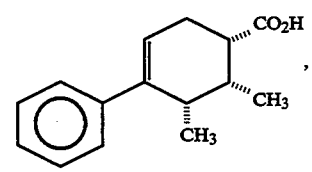 VIII

,

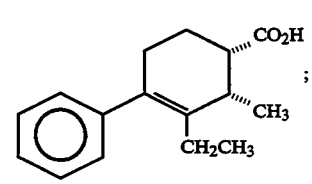 IX

;

wherein R is selected from H, alkyl, alkenyl, acyl and benzyl; and wherein the compound is present as the free acid, a pharmaceutically acceptable salt, or an ester of the free acid.

5. A method according to claim 4, wherein R is H or CH$_3$.

6. A method according to claim 4, wherein the compound is administered with a pharmaceutically acceptable carrier.

7. A method of producing weight loss in warm blooded animals, comprising administering orally or by subcutaneous injection to the animal an effective amount of the (+), the (−) or the (±) form of a compound of formula

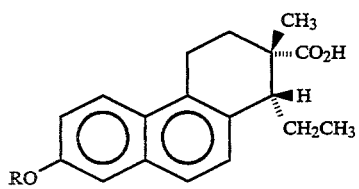

wherein R is selected from H and CH$_3$; and wherein said compound is present as the free carboxylic acid, a pharmaceutically acceptable salt, or an ester of the carboxylic acid.

8. A method of suppressing the appetite of a warm blooded animal, comprising administering orally or by subcutaneous injection to the animal an effective amount of the (+), the (−) or the (±) form of a compound of formula

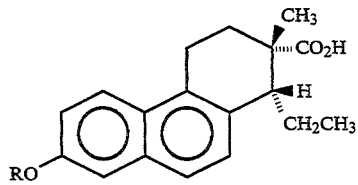

wherein R is selected from H and CH$_3$; and wherein said compound is present as the free carboxylic acid, a pharmaceutically acceptable salt, or an ester of the carboxylic acid.

* * * * *

UNITED STATES PATENT AND TRADEMARK OFFICE
CERTIFICATE OF CORRECTION

PATENT NO.    :   5,420,161
DATED         :   May 30, 1995
INVENTOR(S)   :   Cal Y. Meyers It is certified that error appears in the above-identified patent and that said Letters Patent is hereby corrected as shown below:

In column 1, line 52, delete "vitro" and replace with --vivo--.

Signed and Sealed this

First Day of August, 1995

Attest:

BRUCE LEHMAN

Attesting Officer

Commissioner of Patents and Trademarks